United States Patent [19]

Hlavinka et al.

[11] Patent Number: 5,205,153

[45] Date of Patent: Apr. 27, 1993

[54] METHOD AND APPARATUS FOR DETECTION OF AIR BUBBLES IN TUBING

[75] Inventors: Dennis J. Hlavinka, Golden; Byron W. Larson, Lakewood, both of Colo.

[73] Assignee: COBE Laboratories, Inc., Lakewood, Colo.

[21] Appl. No.: 825,657

[22] Filed: Jan. 23, 1992

[51] Int. Cl.⁵ .......................................... G01N 29/002
[52] U.S. Cl. ...................... 73/79.03; 73/64.53
[58] Field of Search ............... 73/19.03, 644, 61.49, 73/61.75, 64.53, 861.28; 128/DIG. 13; 604/65, 67

[56] References Cited

U.S. PATENT DOCUMENTS

| | | | |
|---|---|---|---|
| 4,235,095 | 11/1980 | Liebermann | 73/19.03 |
| 4,418,565 | 12/1983 | St. John | 73/19.03 |
| 4,607,520 | 8/1986 | Dam | 73/19.03 |
| 4,651,555 | 3/1987 | Dam | 73/19.03 |
| 4,722,224 | 2/1988 | Scheller et al. | 73/599 |

Primary Examiner—Tom Noland
Assistant Examiner—Nashmiya N. Ashraf
Attorney, Agent, or Firm—Beaton & Swanson

[57] ABSTRACT

A method and apparatus for assisting in the detection of bubbles in a fluid stream such as an intravascular line. Tubing having ribbing or other texturing spaced along the longitudinal axis to enhance signal transmission characteristics and to increase the number of signals intercepted by a passing bubble, is placed between an ultrasonic or other transmitter and detector. In other embodiments, bubbles are concentrated into a detection zone by a centrifugator or are concentrated and recirculated in a detection zone by an eddy-producing protrusion in the fluid stream.

17 Claims, 2 Drawing Sheets

METHOD AND APPARATUS FOR DETECTION OF AIR BUBBLES IN TUBING

BACKGROUND OF THE INVENTION

A wide variety of medical procedures utilize an intravascular line to infuse or withdraw blood or fluid from the human body. For example, infusion pumps are commonly used for the controlled infusion of fluid or medication through an intravascular line into a patient's bloodstream.

Many intravascular procedures relate to the extracorporeal treatment of blood, such as blood oxygenation, blood component separation and blood cleansing. Some of these procedures include rather extensive manipulation of the blood and its components. For example, hemodialysis is typically performed by withdrawing the blood via a tube that taps the patient's vascular system, transporting the blood through the tube to a dialyzer, purifying the blood with the dialyzer, transporting the treated blood through another tube from the dialyzer back to the patient, and replacing the treated blood back into the vascular system of the patient. This tube or blood set may also provide for other necessary functions such as pressure monitoring, temperature sensoring, flow detection and blood pumping. Each of these functions may require one or more blood line features such as valves or other fittings.

These procedures can introduce air into the blood line in a variety of ways. One of the most dangerous ways is by a leak in the tubing or a fitting connection. This can introduce a large volume of air which can pass into the bloodstream and cause an embolism or other life-threatening condition.

Many hemodialysis and other intravascular techniques use a device to detect air in the venous tubing before it flows into the patient. Such devices generally rely on the measurement and processing of variations in the optical or ultrasonic characteristics of the fluid in the tubing. The optical devices include a light element that shines light into the fluid flow through the transparent tubing wall. A photocell on the other side of the tubing measures the transmitted light to determine the transmissibility of the fluid, or a photocell on the same side of the tubing measures the reflected light to determine the reflectivity of the fluid. The system can be calibrated to detect and identify predictable transmissibility or reflectivity variances caused by air bubbles.

In the case of ultrasonic devices, which are among the most prevalent of air detection devices used with hemodialysis machines, a segment of the blood set is clamped between ultrasonic transducers that send ultrasonic signals through the blood set wall, through the flowing fluid, and through the opposite blood set wall. The blood without air bubbles has a fairly consistent and predictable transmissibility to the ultrasonic signal. Therefore, any variations in the received signal caused by air bubbles (or even foreign particulates, for that matter) can be detected, processed and measured against the normal signal. Variances exceeding a predetermined absolute threshold, or a predetermined cumulative threshold over a period of time, are deemed to represent an unacceptably high air level. The transducer is coupled with an alarm to warn the operator of the high air level and is also electronically connected to a clamp or other device to occlude the tube and stop the blood pump to prevent the detected air from flowing into the patient.

Due to a variety of factors, the sensitivity of existing air bubble detectors is not always as high as desired. Therefore, the alarm thresholds are typically set conservatively low. This protects the patient but also causes a high number of false alarms. The prior art approach to improving the sensitivity of air bubble detectors has relied largely on making modifications to the electronic circuitry that analyzes the received signals. See, for example, the systems that accumulate signal variances over a period of time and compare the accumulated variances against predetermined thresholds, that are described in U.S. Pat. Nos. 4,341,116 by Bilstad, 3,935,876 by Massie, 4,651,555 by Dam, and 4,487,601 by Lindeman.

One drawback to the approach of increasing the sensitivity of the detector by modifying the electronic circuitry that processes the received signal, is that this approach requires replacing or modifying the circuitry on existing machines that are in use.

Accordingly, there is a need for an approach to increasing the sensitivity of an air bubble detector without modifying the transducers or electronic circuitry of the existing devices. Preferably, the modification would be inexpensive and effective, and a given modification could be interchangeable with a variety of other modified or unmodified versions depending on the sensitivity desired in particular applications.

SUMMARY OF THE INVENTION

The present invention is a method and apparatus for increasing the sensitivity of ultrasonic or other air bubble detection systems that operate on the principle of transmitting a signal into a fluid stream and monitoring variances in the transmissibility of the signal. In a preferred embodiment, the improved sensitivity is obtained by shaping the portion of the tubing into which the signal is transmitted. The shaped tubing has at least one circumferential groove that is recessed from the transducers, two adjacent grooves being separated by contact areas that are in contact with the transducers. The grooves reduce the area of contact between the transducers and the tubing to increase the percentage loss of the transmitted signal for a given sized air bubble. Further, the multiple contact areas divide up the signal to allow multiple opportunities for detecting air as the air passes the transducers. The combination of reduced contact area between the transducers and the tubing and multiple contact areas along the tubing axis has been found to significantly increase the sensitivity of the air bubble detector.

An important advantage to this approach to increasing air bubble detector sensitivity is that tubing sets modified in this manner can be used with existing air detection devices without any change to the transducers or signal processing circuitry. In addition, the tubing sets can be made in a variety of interchangeable configurations depending on the sensitivity desired for particular applications.

In another embodiment, the tubing is molded or a fitting is introduced into the tubing interior such that an eddy is created in the fluid stream which concentrates air bubbles into a detection zone and causes multiple passes of the air bubbles through the detection zone. In yet another embodiment, a centrifugator such as a turbine blade is placed in the fluid stream to spin the fluid about the longitudinal axis of the tubing, so that the higher density liquid is thrown toward the tubing wall while the lower density air bubbles tend to concentrate along the tubing longitudinal axis where they are easiest to detect. As in the first embodiment, these embodiments may be designed for use with existing machines without any alteration to the transducers or electronic circuitry.

All the embodiments herein may be used in combination with an alarm and shutoff system such as an electronically operated clamp to occlude the tubing and a switch to shut off the pump in order to prevent detected air from entering the patient. They may also include circuitry or programmable logic to accumulate detected signal variances over a period of time and to compare the accumulated variances against predetermined thresholds or against thresholds that are based in part on the measurement of the received signal over some preceding time period. Although the invention is described primarily with reference to an air detector system that uses ultrasonic signals, it should be appreciated that the same approaches are applicable to air detectors that use optical principles or any other principle that transmits a signal into the fluid system.

DESCRIPTION OF THE PREFERRED EMBODIMENTS

Figure 1:
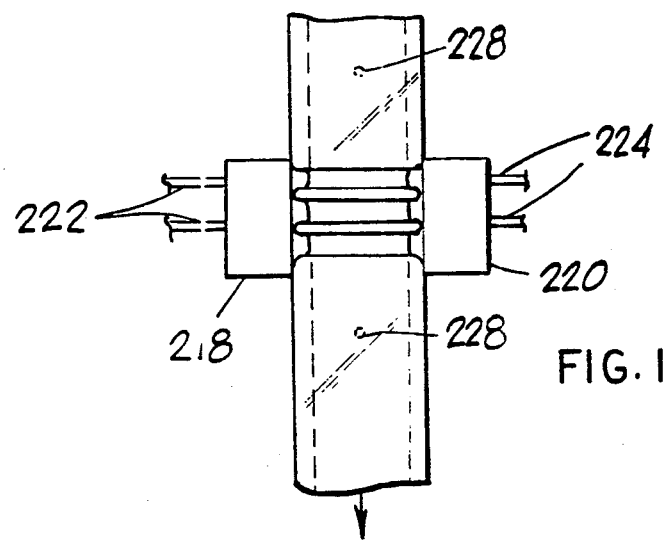
FIG. 1 shows a side elevational view of an embodiment of the present invention coupled with a signal transmitter and receiver.
Figure 2:
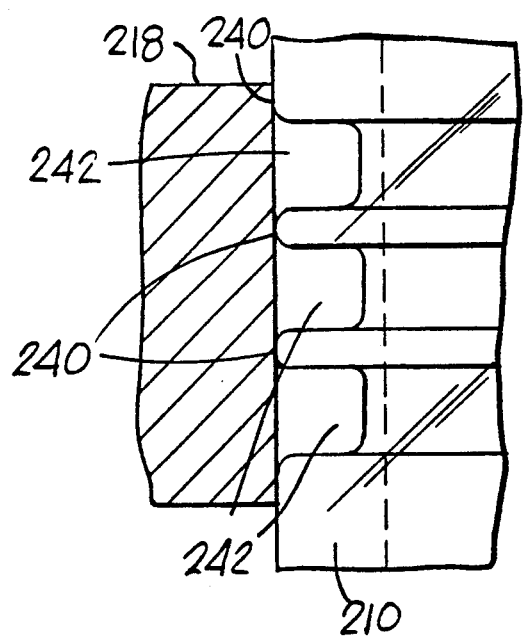
FIG. 2 shows a detail of a side elevational view of the embodiment of FIG. 1.

A preferred embodiment of the invention is shown in FIGS. 1 and 2. The invention 210 includes a length of tubing having a modified section which may be formed using heat molding techniques or by otherwise modifying the tubing after it has been extruded. The modified portion is clamped between an ultrasonic transmitter 218 and receiver 220. The transmitter 218 and receiver 220 each have a pair of leads 222 and 224, respectively, which are in electrical communication with a circuit or programmable element (not shown) to control the transmitted signal and to process the received signal. A signal is transmitted from the transmitter 218 to the receiver 220. Fluid flows through the tubing 210 in the direction of the arrows. Shown within the fluid is a set of bubbles 228.

The tubing 210 is ribbed or grooved in the circumferential direction, along the modified portion. As shown best in FIG. 2, the ribbing includes a plurality of individual ribs 240 extending in the circumferential direction around the tubing 210, each of which is separated from the adjacent rib by a recessed portion 242. The head of the transmitter 218 is applied to the ribs 240, thereby leaving spaces between the transmitter and the tubing at the recessed portions 242. The signal is transmitted from the transmitter 218, into the ribs 240 in contact with the transmitter, and through the wall of the tubing 210 into the fluid. The recessed portions are virtually ineffective in transmitting any of the signal.

The opposite side of the tubing 218 where the tubing contacts the receiver 220 may also be ribbed in the same way as the tubing in contact with the transmitter. Alternatively, the tubing wall in contact with the receiver may be left unribbed. It has been found that leaving the tubing wall in contact with the receiver unribbed may result in better signal transmission. In that configuration, the ribs 240 run circumferentially through only the portion of the tubing 210 that is in contact with the transmitter 218.

Figure 3:
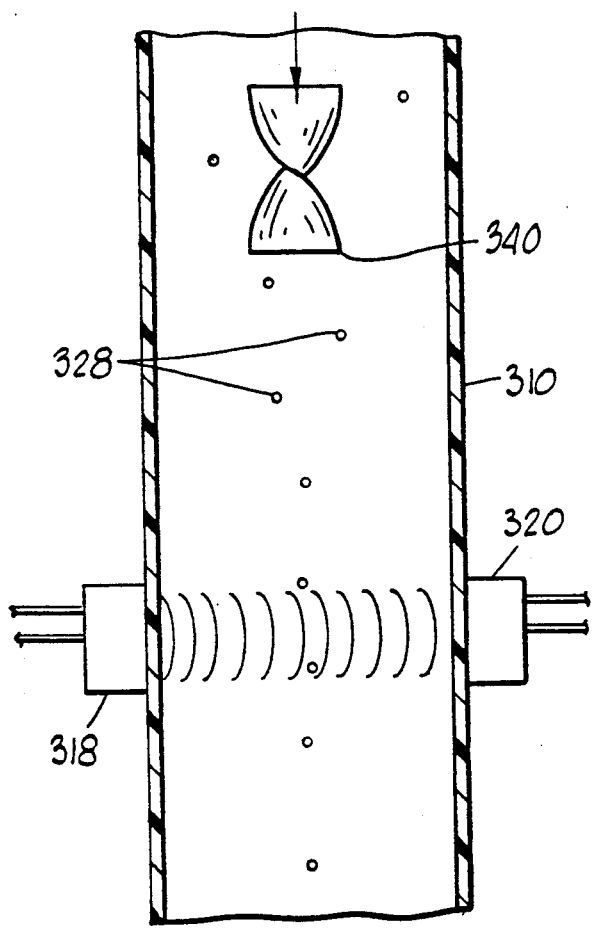
FIG. 3 shows a side elevational view of another embodiment of the present invention.

Another embodiment is shown in FIG. 3 in which the fluid stream is centrifugated to center the air bubbles for detection. The tubing 310 has an implanted centrifugating device 340 such as a vane that spins within the tubing to spiral the fluid stream downstream. The ultrasonic transmitter 318 and receiver 320 are located sufficiently downstream such that the spinning fluid stream centralizes the air bubbles 328 by the time they pass. It has been found that air bubbles may be more easily detected at the center of the stream than at most other locations in the stream. Therefore, this arrangement enhances the detection of the bubbles. The centrifugation arrangement may also include a mechanism for drawing off the concentrated bubbles. Further, the centrifugation arrangement may be used in combination with the ribbed tubing arrangement described above. When the centrifugation arrangement is used in combination with the ribbed tubing, the sensitivity of the detector is improved because the signal transmission through the tubing is improved, because there are multiple opportunities to detect the air as it passes the ribs, and because the bubbles are concentrated into a region where they are easier to detect.

Figure 4:
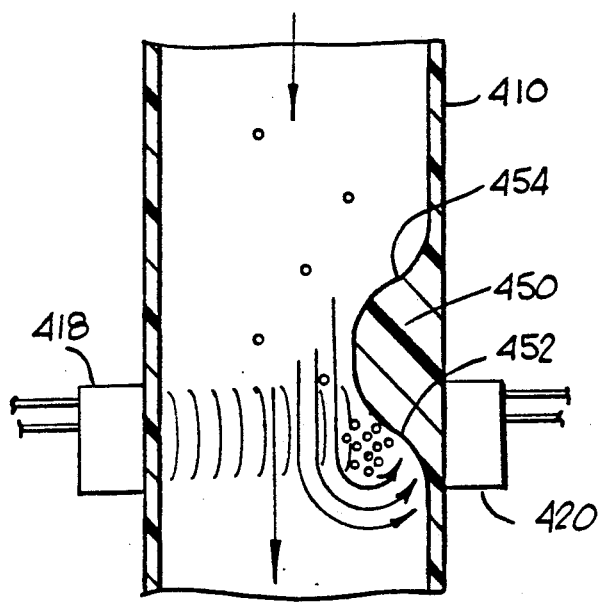
FIG. 4 shows a side elevational view of another embodiment of the present invention.

Another embodiment of the invention is shown in FIG. 4 in which an obstacle is placed in the fluid stream to create an eddy that concentrates and recirculates bubbles for detection. The device includes tubing 410 having an interior protrusion 450 extending from the interior wall into the fluid stream. The protrusion has an upstream side 454 and a downstream side 452. In the preferred embodiment shown in the figure, the protrusion 450 is on one part of the interior wall, but it should be appreciated that the protrusion could extend around the entire circumferential interior wall or any portion thereof. Located slightly downstream from the protrusion 450 are the ultrasonic transmitter 418 and receiver 420.

In operation, the fluid stream speeds up and passes through the constriction caused by the protrusion 450. On the downstream side 452 of the protrusion 450, the fluid forms an eddy which tends to collect the lighter bubbles and cause them to recirculate past the transmitter 418 and receiver 420. Therefore, this embodiment improves the sensitivity of the detector by both concentrating and recirculating the bubbles in the detection zone. As in the case of the centrifugating embodiment, this eddy embodiment may be used in combination with the ribbed tubing embodiment described above.

We claim:

1. An apparatus to engage a device for detecting bubbles in a fluid stream, the device having a transmitting transducer for transmitting signals into the fluid and a receiving transducer for receiving signals from the fluid, the apparatus comprising a channel with an interior surface in contact with the fluid and an exterior surface in contact with the transducers, the exterior surface having at least one portion that is recessed relative to an unrecessed portion, so that at least one of the transducers contacts the unrecessed portion and is adjacent to but not in contact with the recessed portion.

2. The apparatus of claim 1, wherein the channel is a tube.

3. The apparatus of claim 2, wherein said recessed portion is to be adjacent to at least the transmitting transducer.

4. The apparatus of claim 1, wherein the recessed portion includes an upstream recessed portion and a downstream recessed portion, the upstream and downstream recessed portions being separated by an unrecessed portion to be in contact with said at least one of the transducers.

5. The apparatus of claim 4, wherein the recessed and unrecessed portions extend circumferentially around the channel.

6. The apparatus of claim 4, wherein the recessed portions include a plurality of recessed portions spaced along a longitudinal axis of the channel and separated by a plurality of unrecessed portions.

7. The apparatus of claim 6, wherein the recessed and unrecessed portions extend circumferentially around the channel.

8. The apparatus of claim 2, wherein the tube includes a portion upstream from the transducers and a portion downstream from the transducers, and a central portion, the central portion being between the upstream portion and downstream portion and being integral with the upstream and downstream portions, and wherein said central portion includes said at least one portion that is recessed.

9. The apparatus of claim 1, further comprising means inside the channel for concentrating the bubbles into a detection zone which receives the transmitted signals.

10. The apparatus of claim 9, wherein the concentrating means is a centrifugator that tends to collect the bubbles along a longitudinal axis of the channel.

11. The apparatus of claim 9, wherein the concentrating means is a protrusion in the interior surface of the channel which causes a bubble-concentrating and recirculating eddy downstream from the protrusion.

12. A method for detecting air in a fluid stream in a channel, comprising placing a segment of the channel adjacent to a transmitting transducer and a receiving transducer, the segment having at least one portion that is recessed relative to an unrecessed portion, so that at least one of the transducers contacts the unrecessed portion of the segment and is adjacent to but does not contact the recessed portion, transmitting a signal from the transmitting transducer into the fluid, and receiving and processing the signal to detect the passage of air in the channel.

13. The method of claim 12, wherein the recessed portions are configured such that the transmitted signal is divided into a plurality of signals spaced along a longitudinal axis of the fluid stream, whereby an air bubble intercepts a plurality of said signals as it passes through the channel.

14. The method of claim 12, further comprising concentrating air into a detection zone in the fluid, transmitting a signal into the detection zone from the transmitting transducer, and receiving and processing the signal to detect the passage of air in the channel.

15. The method of claim 14, wherein the concentrating step is by centrifuging the fluid about a centrifugal axis so that air concentrates on the centrifugal axis.

16. The method of claim 14, wherein the concentrating step includes both recirculating and concentrating the air in the detection zone.

17. The method of claim 16, wherein the concentrating and recirculating step is by an eddy-causing obstacle in the fluid stream.

* * * * *